United States Patent [19]

Mizejewski

[11] Patent Number: 5,674,842

[45] Date of Patent: Oct. 7, 1997

[54] GROWTH INHIBITORY PEPTIDE

[75] Inventor: Gerald J. Mizejewski, Clifton Park, N.Y.

[73] Assignee: Health Research, Incorporated, Albany, N.Y.

[21] Appl. No.: 329,506

[22] Filed: Oct. 26, 1994

[51] Int. Cl.$^6$ .................... A61K 38/17; C07K 14/435
[52] U.S. Cl. ............................................. 514/12; 530/324
[58] Field of Search ................................. 530/350, 399, 530/324; 514/2, 12; 435/69.1

[56] References Cited

U.S. PATENT DOCUMENTS

| | | | |
|---|---|---|---|
| 4,740,461 | 4/1988 | Kaufman | 435/69.1 |
| 4,753,879 | 6/1988 | Rosa et al. | 435/172.3 |
| 4,766,075 | 8/1988 | Goeddel et al. | 435/240.2 |
| 4,853,330 | 8/1989 | Goeddel et al. | 435/226 |
| 4,914,027 | 4/1990 | Knapp et al. | 435/69.6 |
| 5,096,696 | 3/1992 | Galanakis | 424/1.1 |
| 5,160,483 | 11/1992 | Postlethwaite | 424/85.1 |
| 5,206,164 | 4/1993 | Tecce et al. | 435/240.2 |
| 5,380,712 | 1/1995 | Ballance et al. | 514/12 |
| 5,384,250 | 1/1995 | Murgita | 435/69.6 |

OTHER PUBLICATIONS

Allen et al., "Purification of alpha–fetoprotein from human cord serum with demonstration of its antiestrogenic activity," *Biochimica et Biophysica Acta*, 1202:135–142 (1993).
Bedo, et al., "Retinoic acid regulates growth hormone gene expression," *Nature*, 339:231–234 (May 18, 1989).
Bennett, et al., "Transformation of alpha–fetoprotein (AFP) to a negative regulator of estrogen–dependent growth by ligands of the steroid/thyroid hormone receptor superfamily," Abstract #1452, *Proceedings of the American Association for Cancer Research*, 34:224 (Mar. 1993).
Conti, et al., "Thyroid hormone effect on α–fetoprotein and albumin coordinate expression by a human hepatoma cell line," *Biochimica et Biophysica Acta*, 1008:315–321 (1989).
Dietrich, "New aspects of steroid homone dependent tumor growth," *Arch. Geschwulstforsch* 60(2):149–160 (1990).
Evans, "The Steroid and Thyroid Hormone Receptor Superfamily," *Science*, 240:889–895 (May 13, 1988).
Garreau, et al., "Phytoestrogrens: new ligands for rat and human α–fetoprotein," *Biochimica et Biophysica Acta*, 1094:339–345 (1991).
Gierthy, et al., "Correlation of *in Vitro* and *in Vivo* Growth Suppression of MCF–7 Human Breast Cancer by 2,3,7,8–Tetrachlorodibenzo–p–dioxin," *Cancer Research*, 53:3149–3153 (Jul. 1, 1993).
Gorin, et al., "The Evolution of α–Fetoprotein and Albumin," *The Journal of Biological Chemistry*, 256(4):1954–1059 (Feb. 25, 1981).
Jacobson, et al., "Inhibition of Estrogen–dependent Breast Cancer Growth by a Reaction Product of α–Fetoprotein and Estradiol," *Cancer Research*, 50:415–420, (Jan. 15, 1990).
Jacobson et al., "Estradiol–Induced Changes in Spectral and Biological Properties of Alpha–Fetoprotein," *Tumor Biology*, 11:104 (1990).

Keel, et al., "Purified Human Alpha Fetoprotein Inhibits Growth Factor–Stimulated Estradiol Production by Porcine Granulosa Cells in Monolayer Culture," *Endocrinology*, 130(6):3715–3717 (1992).
Keel, et al., "Purified human α–fetoprotein inhibits follicle–stimulating hormone–stimulated estradiol production by porcine granulosa cells in culture," *Molecular and Cellular Endocrinology*, 94:21–25 (1993).
Mizejewski, et al., "Stability of Complex Formation Between Estradiol and Murine Alpha–Fetoprotein," Abstract #7150, *Clinical Research*, (Spring 1977).
Mizejewski, et al., "Estradiol–activated α–fetoprotein suppresses the uterotropic response to estrogens," *Proc. Natl. Acad. Sci. USA*, 80:2733–2737 (May 1983).
Mizejewski, et al., "New Insights into AFP Structure and Function: Potential Biomedical Applications," in *Alha–Fetoprotein and Congenital Disorders*, Mizejewski, et al., Eds. Academic ress, Inc. New York, N.Y. p. 5–34 (1985).
Mizejewski, et al., "Studies of the Intrinsic Antiuterotropic Activity of Murine Alpha–Fetoprotein," *Tumour Biology*, 7:19–36 (1986).
Mizejewski, et al., "Alpha–Fetoprotein is a Dual Regulator of Growth in Estrogen–Responsive Tissues," in *Biological Activities of Alpha$_1$–Fetoprotein*, vol. I, Mizejewski, et al., Eds., CRC Press, Inc., Boca Raton, FL, pp. 71–82 (1987).
Mizejewski, et al., "AFP Modification of Biologic Response in Estrogen–Sensitive Tissues: Use of *In Vivo* and *In Vitro* Models," in Biological Activities of Alpha$_1$–Fetoprotein, vol. II, Mizejewski, et al., Eds., CRC Press, Inc., Boca Raton, FL, pp. 59–74 (1989).
Mizejewski, et al., "Alpha–fetoprotein can regulate growth in the uterus of the immature and adult ovariectomized mouse," *J. Reprod. Fert*, 85:177–185 (1989).
Mizejewski, et al., "Separation of the Estrogen–Activated Growth–Regulatory Forms of Alpha–Fetoprotein in Mouse Amniotic Fluid," *Biology of Reproduction*, 42:887–898 (1990).
Mizejewski, "An Apparent Dimerization Motif in the Third Domain of Alpha–fetoprotein: Molecular Mimicry of the Steroid/Thyroid Nuclear Receptor Superfamily,".

(List continued on next page.)

(List continued on next page.)
Marianne P. Allen

*Attorney, Agent, or Firm*—Nixon, Hargrave, Devans & Doyle LLP

[57] ABSTRACT

The subject invention provides non–naturally occurring peptides capable of inhibiting growth factor–stimulated growth of cells. The peptide can be utilized to inhibit growth factor–stimulated growth, such growth factors including, for example, gonadotropins, peptide hormones, synthetic growth factors, and ligands, the ligand having a receptor that is a member of the steroid/thyroid hormone/vitamin receptor superfamily. Also provided are DNA sequences encoding the peptides and methods of producing and using the peptides.

2 Claims, No Drawings

OTHER PUBLICATIONS

Morinaga, et al., "Primary structures of human α-fetoprotein and its mRNA," *Proc. Natl. Acad. Sci. USA*, 80:4604–4608 (Aug. 1983).

Nishi, et al., "Estrogen–Binding Site of Rat Alpha–Fetoprotein," *Tumor Biology*, 14:234 (1993).

Nishi, et al., "Localization of the estrogen–binding site of α-fetoprotein in the chimeric human–rat proteins," *Proc. Natl. Acad. Sci. USA*, 88:3102–3105 (Apr. 1991).

Numez, et al., "The Physicochemical and Biological Properties of Alpha–Fetoprotein Depend of its Ligand Environment," *J. Nucl. Med. Allied Sci.*, 33 (Suppl. to No. 3):18–26 (1989).

Rosebrock, et al., "Immunoprecipitation Assay of Alpha–fetoprotein Synthesis by Cultured Mouse Hepatoma Cells Treated with Estrogens and Glucocorticords," *Differentiation*, 19:168–178 (1981).

Savu, et al., "Mouse $\alpha_1$–Fetoprotein and Albumin," *The Journal of Biological Chemistry*, 256(18):9414–9418 (Sep. 25, 1981).

Sonnenschein, et al., "Growth Inhibition of Estrogen–Sensitive tumor Cells in Newborn Rats. Probable Role of Alpha–Fetoprotein," *J. Natl. Can. Inst.*, 63(3):835–841 (Sep. 1979).

Sonnenschein, et al., "Age–Dependent Growth Inhibition of Estrogen–Sensitive Rat Mammary Tumors. Probable Role of Alpha–Fetoprotein," *J. Natl. Can. Inst.*, 64(5):1141–1146 (May 1980).

Sonnenschein, et al., "Growth Inhibition of Estrogen–Sensitive Rat Mammary Tumors. Effect of an Alpha–Fetoprotein–Secreting Hepatoma" *J. Natl. Can. Inst.*, 64(5):1147–1152 (May 1980).

Soto, et al., "Control of growth of estrogen–sensitive cells: Role for α–fetoprotein," *Proc. Natl. Acad. Sci. USA*, 77(4):2084–2087 (Apr. 1980).

Wahli, et al., "Superfamily of seroid nuclear receptors: positive and negative regulators of gene expression," *The FASEB Journal*, 5:2243–2249 (Jun. 1991).

Wan, et al., "The effects of retinoic acid on the expression of α–fetoprotein and albumin genes in rat hepatoma cell lines," *Differentiation*, 50:107–111 (1992).

GROWTH INHIBITORY PEPTIDE

FIELD OF THE INVENTION

This invention is directed to a peptide, and more particularly to a non-naturally occurring peptide capable of inhibiting the growth of cells stimulated by growth factors. The invention also relates to DNA coding for this peptide and vectors and methods for producing the peptide.

BACKGROUND OF THE INVENTION

The nucleotide and amino acid sequences of mouse alpha-fetoprotein (AFP) and human AFP have been published (Gorin, M. B. et al., "The Evolution of α-Fetoprotein and Albumin", J Biol Chem 256:1954–1959 (1981); Morinaga, T. et al., "Primary Structures of human α-Fetoprotein and its mRNA", PNAS 80:4604–4608 (1983)). AFP is a glycoprotein produced during gestation, initially by the fetal yolk sac and then the fetal liver. AFP is a major serum protein constituent of the fetal plasma throughout gestation. However, upon parturition, the gene for AFP is repressed and its serum concentration diminishes to a negligible level. While a complete understanding of the physiological role of AFP is not yet available, the protein does display osmotic and carrier properties similar to albumin. Nevertheless, the reason for its unique existence during fetal development remains unclear.

Studies have shown that when AFP is incubated with a molar excess of the ligand estradiol ($E_2$), the AFP undergoes a change in conformation. This conformational change can be demonstrated spectrophotometrically by the method of difference spectrum (Jacobson, H. et al., "Estradiol-Induced Changes in Spectral and Biological Properties of Alpha-Fetoprotein", Tumour Biology 11:104 (1990)). In this transformed state, AFP inhibits growth of steroid stimulated tissues, including estrogen-stimulated breast cancer growth (Jacobson, H. I. et al., "Inhibition of Estrogen-dependent Breast Cancer Growth by a Reaction Product of α-Fetoprotein and Estradiol", Cancer Research 50:415–420 (1990)). This biological property is not present in native (untransformed) AFP. The anti-estrogenic growth activity was first demonstrated with murine AFP isolated from mouse amniotic fluid (Mizejewski, G. J. et al., "Estradiol-activated α-fetoprotein suppresses the uterotropic response to estrogens", PNAS 80:2733–2737 (1983); Mizejewski, G. J. et al., "Studies of the Intrinsic Antiuterotropic Activity of Murine Alpha-Fetoprotein", Tumour Biology 7:19–36 (1986); Mizejewski, G. J. and A. S. Warner, "Alpha-fetoprotein can regulate growth in the uterus of the immature and adult ovariectomized mouse", J Reprod Fert 85:177–185 (1989)). In an attempt to understand this transformation and how AFP reacts with estrogen, the estrogen-binding site of alpha-fetoprotein in a chimeric human/rat protein was determined (Nishi, S. et al., "Localization of the estrogen-binding site of α-fetoprotein in the chimeric human-rat proteins", PNAS 88:3102–3105 (1991)).

Recently a procedure for purification of human AFP from pooled human cord sera was published (Allen, S. H. G. et al., "Purification of alpha-fetoprotein from human cord serum with demonstration of its antiestrogenic activity", Biochim Biophys Acta 1202:135–142 (1993)). Human AFP was similar to mouse AFP in its ability to be transformed by incubation with estradiol to an inhibitor of estrogen-stimulated growth of mouse uterus.

Estrogen is a growth factor that has a receptor which is a member of the steroid/thyroid hormone/vitamin receptor superfamily. Examples of other receptors in the superfamily include receptors for androgen, progesterone, vitamin-D, retinoic acid, retinol, tri-iodothyronine, glucocorticoids (such as hydrocortisone), and mineralcorticoid. (For a discussion of the receptor superfamily itself, see Evans, R. M., "The Steroid and Thyroid Hormone Receptor Superfamily", Science 240:889–895 (1988); Wahli, W. and Martinez, E., "Superfamily of steroid nuclear receptors: positive and negative regulators of gene expression", FASEB 5:2243–2249 (1991).)

The transformation of AFP by estrogen, and the presence of the receptor for estrogen in the superfamily, led researchers to explore the possibility that other ligands having receptors that are members of the superfamily could similarly transform AFP to an inhibitor of growth. Bennett et al. have shown that other ligands having receptors in the steroid/thyroid hormone/vitamin receptor superfamily also transform AFP to an inhibitor of estrogen-stimulated growth of cells (Bennett, J. A. et al., "Transformation of alpha-fetoprotein (AFP) to a negative regulator of estrogen-dependent growth by ligands of the steroid/thyroid hormone receptor superfamily", Abstract #1452, Proc. of Am. Assoc. for Cancer Research 34:244 (1993)).

Estrogen stimulates the growth of breast cancer cells. These other ligands discussed by Bennett et al. likewise stimulate the growth of other cells. For example, androgen stimulates the growth of prostate cancer cells. The purpose of the subject invention was to determine whether substances other than transformed full length AFP could inhibit the growth of cells, the growth of such cells being stimulated by growth factors, including those ligands whose receptors are members of the steroid/thyroid hormone/vitamin receptor superfamily.

SUMMARY OF THE INVENTION

It is thus an object of the subject invention to provide a peptide capable of inhibiting the growth of cells stimulated by growth factors. Preferably, the peptide of the subject invention is capable of inhibiting growth stimulated by ligands whose receptors are members of the steroid/thyroid hormone/vitamin receptor superfamily, more particularly steroid-stimulated growth such as by estrogen. The subject invention thus provides a non-naturally occurring peptide having an amino acid sequence consisting essentially of SEQ ID NO: 1:

Leu Ser Glu Asp Lys Leu Leu Ala Cys Gly Glu Gly Ala Ala Asp
Ile Ile Ile Gly His Leu Cys Ile Arg His Glu Met Thr Pro Val
Asn Pro Gly Val.

In another embodiment, the peptide of the subject invention is a non-naturally occurring peptide having growth inhibitory activity similar to a second peptide, the second peptide having an amino acid sequence consisting essentially of SEQ ID NO: 1.

Having thus identified the peptides of the subject invention, expression systems are provided for production of the peptides using recombinant DNA technology. An expression vector (such as a plasmid) is thus provided by the subject invention which includes DNA encoding the non-naturally-occurring peptide, and which further includes suitable regulatory elements positioned within the expression vector relative to the DNA encoding the peptide so as to effect expression of the peptide in a suitable host cell. A host cell, such as a bacterial cell, is genetically modified to include the expression vector DNA and regulatory elements, and when the host cell is cultured the peptide is expressed and can be recovered. Purified DNA encoding the peptide, which can be contained in the plasmid, is also included in the scope of the subject invention.

The invention also provides a method of inhibiting growth factor-stimulated growth of cells. The method comprises selecting a sample having cells therein capable of growth factor-stimulated growth. These cells are contacted with the peptide of the subject invention, thereby inhibiting growth factor (i.e., asteroid such as estrogen)-stimulated growth of the cells.

DETAILED DESCRIPTION OF THE INVENTION

The invention provides a non-naturally occurring peptide having an amino acid sequence consisting essentially of SEQ ID NO: 1:

Leu Ser Glu Asp Lys Leu Leu Ala Cys Gly Glu Gly Ala Ala Asp
Ile Ile Ile Gly His Leu Cys Ile Arg His Glu Met Thr Pro Val
Ash Pro Gly Val.

The invention further provides a non-naturally occurring peptide having growth inhibitory activity similar to a second peptide, the second peptide having an amino acid sequence consisting essentially of SEQ ID NO: 1.

As defined herein, the peptides of the subject invention are intended to cover non-naturally occurring peptides having growth inhibitory activity similar to the peptide represented by SEQ ID NO: 1. Growth inhibitory activity can be determined by any suitable means known in the art. For example, inhibition of estrogen-stimulated growth can be assayed as discussed in Examples 2 and 3 below. Inhibition of diethylstilbestrol (DES)-stimulated growth can be assayed as discussed in Example 4. Inhibition of hydrocortisone (HC)-stimulated growth can be assayed as discussed in Example 5, and inhibition of human chorionic gonadotropin (HCG)-stimulated growth can be assayed as discussed in Example 6.

The peptides of the subject invention thus include those consisting essentially of SEQ ID NO: 1 as well as those consisting essentially of fragments of SEQ ID NO: 1 having such growth inhibitory activity. Furthermore, substitutions, additions, deletions, and other alterations of the DNA or amino acid sequences described herein that result in a peptide with the capability of inhibiting such growth factor-stimulated growth of cells are intended to be covered herein. This would include naturally-occurring allelic variations and recombinant variations, such as site-directed mutagenesis.

Growth factors, as used herein, include cell signalling molecules which mediate cellular multiplication and proliferation. Such growth factors include, for example, the family of gonadotropins (including HCG, follicle-stimulating hormone (FSH), luteinizing hormone (LH), and thyroid-stimulating hormone (TSH)), naturally-occurring peptide hormones (such as kinins, which include angiotensin, neuromedin, neurotensin, bradykinin, and substance P), ligands whose receptors are members of the steroid/thyroid hormone/vitamin receptor superfamily (for example, estrogen, androgen, progesterone, vitamin-D, retinoic acid, retinol, tri-iodothyronine, glucocorticoid, and mineralcorticoid), and synthetic growth factors such as DES (a synthetic estrogen) and phorbol esters.

Purified DNA is also provided consisting essentially of DNA coding for a non-naturally occurring peptide, the peptide having an amino acid sequence consisting essentially of SEQ ID NO: 1:

Leu Ser Glu Asp Lys Leu Leu Ala Cys Gly Glu Gly Ala Ala Asp
Ile Ile Ile Gly His Leu Cys Ile Arg His Glu Met Thr Pro Val
Ash Pro Gly Val.

Purified DNA is further provided consisting essentially of DNA coding for a non-naturally occurring peptide, the peptide having growth inhibitory activity substantially similar to a second peptide. The second peptide has an amino acid sequence consisting essentially of SEQ ID NO: 1.

The peptide of the present invention is preferably produced in purified form by conventional techniques using synthetic peptide chemistry in a peptide synthesizer or using recombinant DNA technology. In recombinant DNA technology, typically the peptide of the present invention is secreted into the growth medium of recombinant *E. coli*. To isolate the peptide, the *E. coli* host cell carrying a recombinant plasmid is propagated, homogenized, and the homogenate is centrifuged to remove bacterial debris. The supernatant is then subjected to sequential ammonium sulfate precipitation. The fraction containing the peptide of the present invention is subjected to gel filtration in an appropriately sized dextran or polyacrylamide column to separate the peptides. If necessary, the peptide fraction may be further purified by HPLC.

The DNA molecule encoding the peptide can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in proper sense orientation and correct reading frame. The vector contains the necessary elements for the transcription and translation of the inserted peptide-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccinia virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK± or KS± (see "Stratagene Cloning Systems" Catalog (1993) from Stratagene, La Jolla, Calif., which is hereby incorporated by reference), pQE, pIH821, pGEX, pET series (see F. W. Studier et. al., "Use of T7 RNA Polymerase to Direct Expression of Cloned Genes," Gene Expression Technology 185 (1990), which is hereby incorporated by reference), and any derivatives thereof. Recombinant molecules can be introduced into cells via transformation, particularly transduction, conjugation, mobilization, or electroporation. The DNA sequences are cloned into the vector using standard cloning procedures in the art, as described by Maniatis et al., *Molecular Cloning: A Laboratory Manual*, Cold Springs Laboratory, Cold Springs Harbor, N.Y. (1982), which is hereby incorporated by reference.

A variety of host-vector systems may be utilized to express the peptide-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translatation).

Transcription of DNA is dependent upon the presence of a promotor which is a DNA sequence that directs the binding of RNA polymerase and thereby promotes mRNA synthesis. The DNA sequences of eucaryotic promotors differ from those of procaryotic promotors. Furthermore, eucaryotic promotors and accompanying genetic signals may not be recognized in or may not function in a procaryotic system, and, further, procaryotic promotors are not recognized and do not function in eucaryotic cells.

Similarly, translation of mRNA in procaryotes depends upon the presence of the proper procaryotic signals which differ from those of eucaryotes. Efficient translation of mRNA in procaryotes requires a ribosomal binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, Methods in Enzymology, 68:473 (1979), which is hereby incorporated by reference.

Promotors vary in their "strength" (i.e. their ability to promote transcription). For the purposes of expressing a cloned gene, it is desirable to use strong promotors in order to obtain a high level of transcription and, hence, expression of the gene. Depending upon the host cell system utilized, any one of a number of suitable promotors may be used. For instance, when cloning in $E.$ $coli$, its bacteriophages, or plasmids, promotors such as the T7 phage promoter, lac promotor, trp promotor, recA promotor, ribosomal RNA promotor, the $P_R$ and $P_L$ promotors of coliphage lambda and others, including but not limited, to lacUV5, ompF, bla, lpp, and the like, may be used to direct high levels of transcription of adjacent DNA segments. Additionally, a hybrid trp-lacUV5 (tac) promotor or other $E.$ $coli$ promotors produced by recombinant DNA or other synthetic DNA techniques may be used to provide for transcription of the inserted gene.

Bacterial host cell strains and expression vectors may be chosen which inhibit the action of the promotor unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in $E.$ $coli$ requires a Shine-Dalgarno (SD) sequence about 7-9 bases 5' to the initiation codon (ATG) to provide a ribosome binding site. Thus, any SD-ATG combination that can be utilized by host cell ribosomes may be employed. Such combinations include but are not limited to the SD-ATG combination from the cro gene or the N gene of coliphage lambda, or from the $E.$ $coli$ tryptophan E, D, C, B or A genes. Additionally, any SD-ATG combination produced by recombinant DNA or other techniques involving incorporation of synthetic nucleotides may be used.

Once the isolated DNA molecule encoding the peptide of the subject invention has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, insect, and the like.

Having thus identified and produced the peptides according to the subject invention, a method of inhibiting growth factor-stimulated growth of cells is provided. The method comprises selecting a sample having cells therein capable of growth factor-stimulated growth, and contacting the sample with the peptide of the subject invention. This inhibits growth factor-stimulated growth of the cells. Cells as used herein encompasses a wide range of cells that can be stimulated in their growth by the growth factors, including cancerous cells such as breast cancer cells (whose growth is stimulated by estrogen) and prostate cancer cells (whose growth is stimulated by androgen).

The details of the subject invention are disclosed more fully below in the context of experimental details.

EXAMPLE 1

A 34-amino acid peptide was synthesized in an Applied Biosystems 431A peptide synthesizer (Foster City, Calif.), the peptide consisting of the following amino acid sequence, SEQ ID NO: 1:

Leu Ser Glu Asp Lys Leu Leu Ala Cys Gly Glu Gly Ala Ala Asp
Ile Ile Ile Gly His Leu Cys Ile Arg His Glu Met Thr Pro Val
Ash Pro Gly Val.

The synthesized 34-mer peptide was analyzed by mass spectrometry and found to contain the predicted molecular mass (3.573 Daltons). A subsequent analysis of the crude peptide by circular dichroism revealed 7% alpha-Helix, 43% beta sheets, and 45% random (coil) turns. The crude peptide was further purified by HPLC to 99.9% purity, and the amino acid composition of the HPLC-purified peptide revealed the presence of all the designated amino acids (except proline and cysteine that cannot be measured). Thus, the major component in the crude synthetic preparation contained the amino acid composition of the peptide intended.

The 34-mer peptide, designated the Growth Inhibitory Peptide (GIP), was subsequently tested for its biological activity in two separate bioassays for inhibition of estrogen-stimulated growth (an in vivo bioassay measuring an estrogen-induced increase in wet weight of the immature mouse uterus in a 24-hour determination; and an in vitro assessment of estrogen-induced foci formation by human MCF-7 breast cancer cells), as well as separate bioassays for inhibition of DES-stimulated growth (an in vivo bioassay measuring a DES-induced increase in wet weight of the immature mouse uterus); inhibition of hydrocortisone-stimulated growth (an in vivo bioassay measuring a hydrocortisone-induced increase in wet weight of the immature mouse spleen); and inhibition of HCG-stimulated growth (an in vivo bioassay measuring an HCG-induced increase in wet weight of the immature mouse ovary). In all assay results for immature mice, each experiment represents data from five individual mice, and in all assay results for adult mice, each experiment represents data from three individual mice.

EXAMPLE 2

An in vivo wet weight bioassay measuring inhibition of estrogen-stimulated growth of uteri was performed. The procedure of Mizejewski et al. was used for the wet weight assay (see Mizejewski, G. J. et al. (1983); Mizejewski, G. J. et al. (1986); Mizejewski, G. J. and A. S. Warner (1989); Mizejewski, G. J. et al., "Separation of the Estrogen-Activated Growth-Regulatory Forms of Alpha-Fetoprotein in Mouse Amniotic Fluid," Biol of Reprod 42:887–898 (1990); and Allen, S. H. G. et al. (1993)).

Briefly, the synthesized powdered peptide was reconstituted in saline (1 mg/ml) to form a stock solution of the GIP. The stock solution was appropriately diluted to provide dosages of 25 to 100 ng/mouse. 0.1 ml of the appropriately diluted GIP was injected intraperitoneally into 15–18 day old Nya:NYLAR female mice. Control mice were injected with saline or other peptides, including a peptide encoded by a portion of the amino acid sequence of albumin and a random 34 amino acid peptide. 1 hour after this first injection, an estrogen challenge of 0.5 micrograms of $E_2$ in 0.1 ml saline was given to determine the change in uterine responsiveness to $E_2$ resulting from exposure to the first injection. 23 hours after the second injection, uteri were dissected, trimmed free of connective tissue and immediately weighed. The uterine wet weights were normalized to mouse body weight (mg uterine weight/g of body weight) to compensate for differences in body weight among litters of the same age. Percent inhibition of estrogen-stimulated uterine growth was calculated as described by Mizejewski et al. (1983).

The results of the wet weight assay for GIP are summarized in Table 1. These data indicate that the 34-mer peptide (GIP) gave inhibition of 33–79% of estrogen-stimulated growth. This inhibition was similar and/or exceeded inhibition of estrogen-stimulated growth obtained with the full-length transformed AFP molecule (20–40% inhibition) (see references cited). The bioassay data for the immature mice was confirmed again on about forty additional repeats and at least ten additional repeats were performed using adult female mice.

The most effective dose of GIP to produce 30–40% growth inhibition in the immature uterus was determined to be 50 ng/mouse, thus being 5-fold more potent than the full-length transformed AFP molecule. As discussed previously, $E_2$ activation of full-length AFP in a test tube prior to inoculation (resulting in transformed AFP) is necessary for the full-length protein to have this inhibitory effect, but proved unnecessary for the GIP (with activity demonstrable at 100 ng/mouse) provided the mouse contains the circulating ligand (estrogen). Furthermore, it was demonstrated that GIP was active in adult cycling mice both with and without the addition of purified human full-length AFP.

Finally, it was demonstrated that other control peptides, a 34-mer anomalous control peptide and a peptide from the carboxy terminal half of bovine serum albumin, showed no effect whatever over the same dose titration range in the immature mouse uterus.

EXAMPLE 3

In an in vitro bioassay, the MCF-7 focus assay was used for preliminary evaluation of the GIP preparation for both estrogenicity and antiestrogenicity. One of the major consequences of human estrogen exposure is induction of cell proliferation and subsequent structural rearrangement of the acini, a process based on the interactions of multiple estrogen dependent gene expressions. The MCF-7 human breast epithelial cell line derived from an adenocarcinoma has been used extensively as a model of estrogen dependent breast cancer, and MCF-7 cultures exhibit estrogen dependent enhanced cell proliferation in vitro and in vivo using xenografts. The estrogen dependent MCF-7 cell proliferation is primarily a postconfluent event which leads to development of multicellular aggregates (foci). These studies have characterized the estrogen dependency of focus development in MCF-7 cultures and demonstrated the usefulness of this system as an assay for estrogenic activity or, by challenging an estrogen stimulation, the antiestrogenic efficacy of a substance. The procedure of Gierthy et al. was used for the MCF-7 assay of the GIP (see Gierthy, J. F. et al., "Correlation of in Vitro and in Vivo Growth Suppression of MCF-7 Human Breast Cancer by 2,3,7,8-Tetrachlorodibenzo-p-dioxin", Cancer Research 53:3149–3153 (1993)).

Briefly, stock MCF-7 cells were suspended in medium (see Gierthy, J. F. et al. 1993) after treatment with trypsin (0.25%) and seeded into 24-well plastic tissue culture plates. The MCF-7 cells were seeded (2 cm²/well) at a density of $10^5$ cells/well in 1 ml of medium, and incubated at 37° C. in a humidified atmosphere containing 5% $CO_2$. The cultures were refed at 24 hours and every 4–5 days thereafter with 2 ml medium supplemented with $1\times10^{-9}M$ 17β-estradiol, a concentration which induces maximum focus development, and various concentrations of GIP ($10^{-8}M$–$10^{-13}M$) in nonestrogenic $DC_5$ medium and estrogenic $DF_5$ medium which contains high levels of bovine alpha-fetoprotein (5% fetal bovine serum supplemented). After 14 days the cultures were fixed with formalin in pH 7.4 buffer (see Gierthy, J. F. et al. 1993) and stained with 1% rhodamine B. Foci were counted by using an automated colony counter modified to magnify the image of the microscopic multicellular foci. The foci retained the red rhodamine B stain to a greater extent than did surrounding monolayer cells, affording appropriate contrast for enumeration.

The results of the MCF-7 assay for GIP are summarized in Table 2. Results were confirmed with additional repeats and indicate that GIP was inhibitory to the $DF_5$ induced foci development to a maximum of 74% over a GIP concentration range of $10^{-10}$ to $10^{-13}M$. It was also found that higher concentrations of GIP were estrogenic, i.e., induced foci development, in the nonestrogenic $DC_5$ environment in a dose responsive manner starting at $10^{-8}M$. Therefore, GIP exhibits a biphasic response which is antiestrogenic at low concentrations and estrogenic at higher concentrations.

EXAMPLE 4

An in vivo wet weight bioassay measuring inhibition of diethylstilbestrol (DES)-stimulated growth was also performed. The procedure of Mizejewski et al. (see previous citations) was used for the wet weight assay. The applicability of the wet weight bioassay for measuring DES-stimulated growth of uteri is disclosed by Korach, K. S. et al., "Estrogenic activity in vivo and in vitro of some diethylstilbestrol metabolites and analogs", Proc Natl Acad Sci U.S.A. 75:468–471 (1978).

Briefly, the synthesized powdered peptide was reconstituted in saline (1 mg/ml) to form a stock solution of the GIP. The stock solution was appropriately diluted to provide dosages of 10 ng to 100 µg/mouse. 0.1 ml of the appropriately diluted GIP was injected intraperitoneally into 15–18 day old Nya:NYLAR female mice. Control mice were injected with saline. 1 hour after this first injection, a DES challenge of 0.5 micrograms of DES in 0.1 ml saline was given to determine the change in uterine responsiveness to DES resulting from exposure to the first injection. 23 hours after the second injection, uteri were dissected, trimmed free of connective tissue and immediately weighed. The uterine wet weights were normalized to mouse body weight (mg uterine weight/g of body weight) to compensate for differences in body weight among litters of the same age. Percent inhibition of DES-stimulated uterine growth was calculated as described by Mizejewski et al. (1983).

The results of the wet weight assay are summarized in Table 3. These data indicate that the 34-mer peptide (GIP) gave inhibition of DES-induced growth in a range of 14–27%. The bioassay data for the immature mice was confirmed again on three additional repeats and a further repeat was performed using adult female mice.

The most effective dose of GIP which produced 27% growth inhibition in the immature uterus was determined to be 10 ng/mouse.

EXAMPLE 5

An in vivo wet weight bioassay measuring inhibition of hydrocortisone (HC)-stimulated growth of the spleen was also performed. The procedure of Mizejewski et al. (see previous citations) was used for the wet weight assay. The applicability of the wet weight bioassay for measuring HC-stimulated growth of the spleen is disclosed by el-Fouhil, A. F. and Turkall, R. M., "Effect of alternate-day hydrocortisone therapy on the immunologically immature rat. I: Effect on blood cell count, immunoglobulin concentrations, and body and organ weights", Toxicologic Pathology 21(4):377–382 (1993).

Briefly, the synthesized powdered peptide was reconstituted in saline (1 mg/ml) to form a stock solution of the GIP. The stock solution was appropriately diluted to provide dosages of 500 ng to 100 µg/mouse. 0.1 ml of the appropriately diluted GIP was injected intraperitoneally into 15–18 day old Nya:NYLAR female mice. Control mice were injected with saline. 1 hour after this first injection, an HC challenge of 0.5 micrograms of HC in 0.1 ml saline was given to determine the change in spleenic responsiveness to HC resulting from exposure to the first injection. 23 hours after the second injection, spleens were dissected, trimmed free of connective tissue and immediately weighed. The spleenic wet weights were normalized to mouse body weight (mg spleenic weight/g of body weight) to compensate for differences in body weight among litters of the same age. Percent inhibition of HC-stimulated spleenic growth was calculated as described by Mizejewski et al. (1983).

The results of the wet weight assay are summarized in Table 4. These data indicate that the 34-mer peptide (GIP) gave inhibition of HC-induced growth in a range of 24–100%. The bioassay data for the immature mice was confirmed again on one additional repeat.

The most effective dose of GIP which produced 100% growth inhibition in the immature spleen was determined to be 1.0 µg/mouse.

EXAMPLE 6

An in vivo wet weight bioassay measuring inhibition of human chorionic gonadotropin (HCG)-stimulated growth of the ovary was performed. The procedure of Mizejewski et al. (see previous citations) was used for the wet weight assay. The applicability of the wet weight bioassay for measuring HCG-stimulated growth of the ovary is disclosed by Mizejewski, G. J., "Human Chorionic Gonadotrophin: Comparative Studies of Ovarian Uptake In Mammals", Comp Biochem Physio 52A:29–34 (1975).

Briefly, the synthesized powdered peptide was reconstituted in saline (1 mg/ml) to form a stock solution of the GIP. The stock solution was appropriately diluted to provide dosages of 10 ng to 100 µg/mouse. 0.1 ml of the appropriately diluted GIP was injected intraperitoneally into 15–18 day old Nya:NYLAR female mice. Control mice were injected with saline. 1 hour after this first injection, an HCG challenge of 2.8 I.U. of HCG in 0.05 ml saline was given to determine the change in ovarian responsiveness to HCG resulting from exposure to the first injection. 23 hours after the second injection, ovaries were dissected, trimmed free of connective tissue and immediately weighed. The ovarian wet weights were normalized to mouse body weight (mg ovarian weight/g of body weight) to compensate for differences in body weight among litters of the same age. Percent inhibition of HCG-stimulated ovarian growth was calculated as described by Mizejewski et al. (1983).

The results of the wet weight assay are summarized in Table 5. These data indicate that the 34-mer peptide (GIP) gave inhibition of HCG-induced growth in a range of 22–100%. The bioassay data for the immature mice was confirmed again on two additional repeats and a further repeat was performed using adult female mice.

The most effective dose of GIP which produced 100% growth inhibition in the immature ovary was determined to be 1 µg/mouse.

Based on these findings, one concludes that the growth inhibitory peptide of the subject invention, when diluted 2,000-fold or more, produces a 30–40% inhibition of estrogen-stimulated growth in the immature mouse uterus, 80% in the adult, and 60–70% inhibition at $10^{-10}$ to $10^{-13}$M peptide concentration in the MCF-7 cell culture assays. Various beneficial characteristics of GIP make it superior to native, full-length transformed AFP as an inhibitor of estrogen-induced growth. One characteristic is that the GIP is used without the need for transformation with a ligand, such as estradiol, assuming there is some estrogen present in the assay system. Furthermore, the 34 amino acid sequence is practical as an inhibitor of growth factor-stimulated growth in general because it can be readily produced with a peptide synthesizer or using recombinant DNA techniques. Additionally, unlike the full-length transformed human AFP preparations, the GIP retains its inhibitory activity in the lyophilized state for at least twelve (12) months. In contrast, the transformed human AFP retains activity for one week or less. Thus, GIP offers significant advantages as an inhibitor of growth factor-stimulated growth over transformed, full-length human alpha-fetoprotein.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

TABLE 1

In Vivo Wet Weight Bioassay Results
(Estrogen-Stimulatd Growth of Uteri)

| Experiment # | Assay | Dose Per Mouse | Percent Growth Inhibition |
|---|---|---|---|
| 1 | immature mouse uterus | 25 ng | 33 |
| 2 | immature mouse uterus | 50 ng | 38 |
| 3 | immature mouse uterus | 50 ng | 37 |
| 4 | immature mouse uterus | 100 ng | 35 |
| 5a | immature mouse uterus | 50 ng | 37 |
| 5b | - added human AFP | 25 ng | 42 |
| 6a | adult mouse uterus | 25 ng | 66 |
| 6b | - added human AFP | 100 ng | 79 |

TABLE 2

In Vitro MCF-7 Assay Results

| Experiment # | Assay | Peptide Molarity | Percent Foci Inhibition |
|---|---|---|---|
| 1 | MCF-7 Cell Culture | $10^{-10}$–$10^{-12}$ | 60–70 |
| 2a | MCF-7 Cell Culture | $10^{-11}$–$10^{-13}$ | 60–74 |
| 2b | - added human AFP | $10^{-12}$ | 40 |
| 3 | MCF-7 Cell Culture | $10^{-11}$–$10^{-13}$ | 50–60 |

TABLE 3

In Vivo Wet Weight Bioassay Results
(DES-Stimulated Growth of Uteri)

| Experiment # | Assay | Dose per Mouse | Percent Growth Inhibition |
|---|---|---|---|
| 1 | immature mouse uterus | 800 ng | 18% |
| 2 | immature mouse uterus | 10 ng | 27% |
| 3 | immature mouse uterus | 100 µg | 14% |
| 4 | immature mouse uterus | 10 µg | 20% |
| 5 | immature mouse uterus | 1 µg | 22% |
| 6 | immature mouse uterus | 100 ng | 25% |

TABLE 3-continued

In Vivo Wet Weight Bioassay Results
(DES-Stimulated Growth of Uteri)

| Experiment # | Assay | Dose per Mouse | Percent Growth Inhibition |
|---|---|---|---|
| 7 | immature mouse uterus | 10 ng | 25% |
| 8 | adult mouse uterus | 100 µg | 25% |
| 9 | adult mouse uterus | 100 ng | 22% |

TABLE 4

In Vivo Wet Weight Bioassay Results
(HC-Stimulated Growth of the Spleen)

| Experiment # | Assay | Dose per Mouse | Percent Growth Inhibition |
|---|---|---|---|
| 1* | immature mouse uterus | 100 µg | 24% |
| 2* | immature mouse spleen | 100 µg | 34% |
| 3 | immature mouse spleen | 100 µg | 67% |
| 4 | immature mouse spleen | 10.0 µg | 76% |
| 5 | immature mouse spleen | 1.0 µg | 100% |
| 6 | immature mouse spleen | 500 ng | 67% |

*These mice received 1.0 µg of HC instead of 0.5 µg.

TABLE 5

In Vivo Wet Weight Bioassay Results
(HCG-Stimulated Growth of the Ovary)

| Experiment # | Assay | Dose per Mouse | Percent Growth Inhibition |
|---|---|---|---|
| 1 | immature mouse ovary | 100 µg | 22% |
| 2 | immature mouse ovary | 10 µg | 94% |
| 3 | immature mouse ovary | 1 µg | 100% |
| 4 | immature mouse ovary | 500 ng | 67% |
| 5 | immature mouse ovary | 250 ng | 56% |
| 6 | immature mouse ovary | 125 ng | 50% |
| 7 | immature mouse ovary | 1 µg | 79% |
| 8 | immature mouse ovary | 100 ng | 70% |
| 9 | immature mouse ovary | 10 ng | 67% |
| 10 | adult mouse ovary | 10 µg | 50% |

What is claimed is:

1. A non-naturally occurring peptide having an amino acid sequence consisting of SEQ ID NO: 1:

Leu Ser Glu Asp Lys Leu Leu Ala Cys Gly Glu Gly Ala Ala Asp
Ile Ile Ile Gly His Leu Cys Ile Arg His Glu Met Thr Pro Val
Asn Pro Gly Val.

2. A composition comprising the peptide of claim 1 and a suitable carrier.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
      ( A ) LENGTH: 34 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x ) PUBLICATION INFORMATION:
- ( A ) AUTHORS: Morinaga, Tomonori
  - Sakai, Masaharu
  - Wegmann, Thomas G.
  - Tamaoki, Taiki
- ( B ) TITLE: Primary Structures of Human Alpha-fetoprotein and its mRNA
- ( C ) JOURNAL: Proc. Natl. Acad. Sci. U.S.A.
- ( D ) VOLUME: 80
- ( F ) PAGES: 4604-4608
- ( G ) DATE: Aug-1983

( x i ) SEQUENCE DESCRIPTION: SEQ ID NO:1:

```
Leu Ser Glu Asp Lys Leu Leu Ala Cys Gly Glu Gly Ala Ala Asp Ile
1               5                   10                  15
Ile Ile Gly His Leu Cys Ile Arg His Glu Met Thr Pro Val Asn Pro
            20                  25                  30
Gly Val
```